United States Patent
Rogers et al.

(10) Patent No.: US 8,245,594 B2
(45) Date of Patent: Aug. 21, 2012

(54) ROLL JOINT AND METHOD FOR A SURGICAL APPARATUS

(75) Inventors: Theodore W. Rogers, Alameda, CA (US); Matthew R. Williams, Walnut Creek, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 715 days.

(21) Appl. No.: 12/342,396

(22) Filed: Dec. 23, 2008

(65) Prior Publication Data
US 2010/0160929 A1  Jun. 24, 2010

(51) Int. Cl.
*B25J 17/02* (2006.01)
(52) U.S. Cl. ........... 74/490.06; 74/490.04; 294/111; 403/53; 414/735; 901/21; 901/29
(58) Field of Classification Search .......... 414/735; 901/28, 29, 21; 74/490.04, 490.05, 490.06; 294/111; 403/53, 58, 113, 114; 606/205, 606/1
See application file for complete search history.

(56) References Cited

U.S. PATENT DOCUMENTS

| | | | |
|---|---|---|---|
| 4,928,546 A * | 5/1990 | Walters | 74/490.06 |
| 6,676,684 B1 | 1/2004 | Morley et al. | |
| 6,817,974 B2 | 11/2004 | Cooper et al. | |
| 7,320,700 B2 | 1/2008 | Cooper et al. | |
| 7,398,707 B2 | 7/2008 | Morley et al. | |
| 2005/0204851 A1 * | 9/2005 | Morley et al. | 74/490.01 |
| 2008/0243064 A1 | 10/2008 | Stahler et al. | |

OTHER PUBLICATIONS

Vertut, Jean and Philippe Coiffet, *Teleoperation and Robotics: Evolution and Development*, English translation Prentice-Hall, Inc., Inglewood Cliffs, NJ, USA, 1986, 332 pages.

* cited by examiner

*Primary Examiner* — Donald Underwood

(57) ABSTRACT

A roll joint utilizes at least one tendon guide surface to guide actuator tendons for distal roll off and on their respective drums on a central shaft of the roll joint. The tendon guide surface turns the actuator tendon in an axial direction in a more compact space than might be required for a pair of pulleys, while using fewer parts with larger features more easily formed on a small scale.

20 Claims, 17 Drawing Sheets

ROLL JOINT AND METHOD FOR A SURGICAL APPARATUS

BACKGROUND OF THE INVENTION

1. Field of the Invention

The present invention relates generally to joints for surgical apparatus used in remote surgery, and more particularly to a roll joint for a surgical apparatus.

2. Description of Related Art

Minimally invasive telesurgical robotic systems increase a surgeon's dexterity when working within an internal surgical site, as well as allow a surgeon to operate on a patient from a remote location. In a telesurgery system, the surgeon is often provided with an image of the surgical site. While viewing a three-dimensional image of the surgical site on a suitable viewer or display, the surgeon performs the surgical procedures on the patient by manipulating master input devices of the system.

The master input devices control the motion of a servomechanically operated surgical instrument. During the surgical procedure, the telesurgical robotic system can provide mechanical actuation and control of a variety of surgical instruments or tools having end effectors such as tissue graspers, needle drivers, or the like. The end effectors allow the surgeon to perform various functions, e.g., holding or driving a needle, grasping a blood vessel, dissecting tissue, or the like, in response to manipulation of the master input devices.

Some surgical tools employ a roll-pitch-yaw mechanism for providing motion three degrees of freedom to an end effector through the use of three rotary joints. The pitch and yaw rotations are typically provided by a wrist mechanism coupled between a shaft of the tool and the end effector, and the roll rotation is typically provided by rotation of the entire shaft of the tool, driven by an actuator coupled to the proximal end of the shaft. At about 90° pitch, the yaw and roll rotational movements overlap, resulting in the loss of one degree of freedom of motion, referred to as a singularity.

Wrist mechanisms have been developed that can provide roll for the end effector distal to the pitch and yaw joints. These prior art roll joints used very small pulleys to transition the roll drive tendons from an axial orientation along the shaft of the surgical instrument to a perpendicular orientation suitable for actuating a rolling joint with an axis substantially parallel to the long axis of the surgical instrument. These pulleys required very small axles, which were limited in load carrying capability and were difficult to assemble. Further, these pulleys consumed a significant volume in the surgical instrument wrist in a manner that conflicts with making use of the same volume to stiffen the structure of the surgical instrument.

SUMMARY OF THE INVENTION

In one aspect, a roll joint, in either a wrist of a surgical instrument of a robotic surgical system, a manually operated surgical instrument, a robotically controlled endoscope, or a manually operated endoscope, utilizes at least one tendon guide surface to guide the actuator tendons for distal roll off and on their respective drums on a central shaft of the roll joint. The tendon guide surface turns the actuator tendon in an axial direction in a more compact space than might be required for a pair of pulleys, while using fewer parts with larger features more easily formed on a small scale.

The roll joint has a longitudinal axis and includes first and second actuator tendons. Each of the tendons includes a distal end.

The roll joint also includes a shaft assembly that in turn includes a shaft. The shaft has a distal end and a proximal end. A proximal direction is defined from the distal end to the proximal end. The distal end of the first actuator tendon is attached to the shaft at a first connection point that is distal to the tendon guide surface. The distal end of the second actuator tendon is attached to the shaft at a second connection point that also is distal to the tendon guide surface. Thus, the first and second actuator tendons are coupled to the shaft.

The roll joint further includes a housing. The housing has the shaft assembly rotatably mounted therein. Thus, the shaft is said to be rotatably mounted in the housing.

In one aspect, the housing includes a plurality of tendon guide channels. In one aspect, each tendon guide channel has a longitudinal axis substantially parallel to the longitudinal axis of the roll joint. The first actuator tendon passes through a first of the plurality of tendon guide channels. The second actuator tendon passes through a second of the plurality of tendon guide channels.

The shaft assembly also includes at least one tendon guide structure, mounted about the shaft. The tendon guide structure is sometimes referred to as a guide structure. The tendon guide structure includes a tendon guide surface. The tendon guide surface guides at least the first actuator tendon onto a drum region of the shaft.

The tendon guide surface is shaped so that the actuator tendon is approximately tangent to the tendon guide surface as the actuator tendon moves onto the tendon guide surface towards the drum and also is approximately tangent to the tendon guide surface as the actuator tendon moves off the tendon guide surface towards the proximal end of the roll joint. The tendon guide surface changes the direction of motion of the actuator tendon from being along the longitudinal axis to the direction of motion of the actuator tendon being around the longitudinal axis and conversely, from being around the longitudinal axis to being along the longitudinal axis.

In another aspect, the shaft assembly also includes a second tendon guide structure that is different from the at least one tendon guide structure. The second tendon guide structure includes a second tendon guide surface. The second tendon guide surface guides the second actuator onto another drum region of the shaft. The another drum region is different from the drum region. The first and second tendon guide structures are, for example, portions of hemispherical structures. The first actuator tendon wraps around the drum in a first direction and the second actuator tendon wraps around the another drum in a second direction. The first direction is opposite to the second direction.

In yet another aspect, the at least one tendon guide surface guides the second actuator tendon onto the drum region of the shaft. The at least one tendon guide structure is, for example, at least a portion of a spherical structure. In this aspect, a housing of the roll joint is coupled to the shaft assembly, and therefore the shaft, by a plurality of arms extending from the housing. The roll joint includes a first tendon guide structure mounted about the plurality of arms and a second tendon guide structure mounted about the housing.

A method for providing distal roll in a wrist of a surgical instrument includes creating a difference in tension in a first actuator tendon and a second actuator tendon. A tail of the first actuator tendon is coupled to the shaft assembly of a roll joint. A tail of the second actuator tendon is also coupled to the shaft of the roll joint. The shaft is included in a shaft assembly rotatably mounted in a housing of the roll joint.

In response to the difference in tension, the first actuator tendon is unwrapped from the shaft, in a first direction and the shaft assembly rotates in the first direction. In response to the shaft assembly rotating, the second actuator tendon is wrapped about the shaft in the first direction. In one aspect, the distal roll is in a roll joint having only a roll degree of freedom. In another aspect, the distal roll is in a roll joint having pitch, yaw, and roll degrees of freedom.

BRIEF DESCRIPTION OF THE DRAWINGS

In the drawings, elements with the same reference numeral are the same or equivalent elements. Also, the first digit of a reference numeral for an element is the figure number of the drawing in which that element first appears.

As used herein, "end effector" refers to an actual working distal part that is manipulable for a medical function, e.g., for effecting a predetermined treatment of a target tissue. For instance, some end effectors have a single working member such as a scalpel, a blade, or an electrode. Other end effectors have a pair or plurality of working members such as forceps, graspers, scissors, or clip appliers, for example.

As used herein, the terms "surgical instrument", "instrument", "surgical tool", or "tool" refer to a member having a working end which carries one or more end effectors to be introduced into a surgical site in a cavity of a patient. The tool is actuatable from outside the cavity to manipulate the end effector(s) for effecting a desired treatment or medical function of a target tissue in the surgical site. The tool typically includes a shaft carrying the end effector(s) at a distal end, and is preferably servomechanically actuated by a telesurgical system for performing functions such as holding or driving a needle, grasping a blood vessel, and dissecting tissue.

DETAILED DESCRIPTION

Figure 1A:
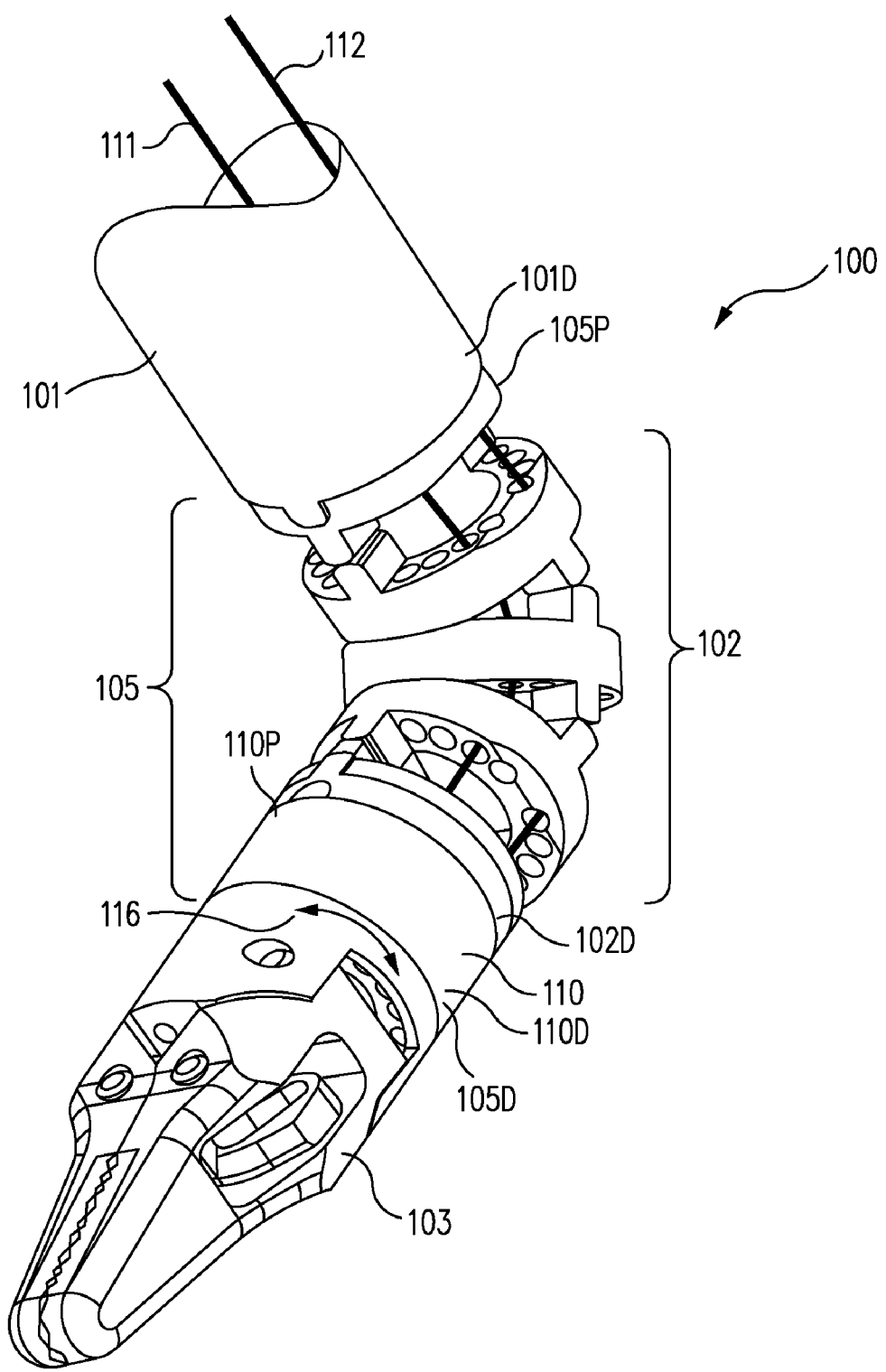
FIGS. 1A, 1B, and 1C are illustrations of a roll joint and the various rotations of an end effector provided by the roll joint without the use of pulleys.

In one aspect, a robotic surgical system includes a surgical instrument 100 (FIG. 1A) that includes a shaft 101. Shaft 101 is coupled to an end effector 103 by a wrist 105 that includes (1) a plurality of joints 102, and (2) a compact and rigid roll joint 110 that rotates in directions 116 around an axis that extends through the longitudinal center line. (See for example, axis 270 in FIG. 2A.) While in this example, roll joint 110 is mounted distally to plurality of joints 102, this is illustrative only and is not intended to be limiting. Roll joint 110 can be used at any locations where the attributes of roll joint 110 are beneficial.

As used herein, distal means a portion of an element furthest removed from the apparatus supporting surgical instrument 100, while proximal means a portion of that element closest to the apparatus. For example, wrist 105 has a proximal end 105P connected to a distal end 101D of shaft 101 and a distal end 105D connected to end effector 103. A proximal end 110P of roll joint 110 is connected to a distal end 102D of plurality of joints 102. Distal end 110D of roll joint 110 is adjacent to end effector 103.

As explained more completely below, two roll actuator tendons 111, 112 are used with roll joint 110 to provide distal roll 116 for end effector 103. An end of actuator tendon 111, sometimes called a tail, is connected to a shaft in roll joint 110, and an end of actuator tendon 112, also sometimes called a tail, is also connected to that shaft.

At least a portion of actuator tendon 111 is wound around the shaft and a portion of actuator tendon 112 is wound around the shaft in the opposite direction. Also, as explained more completely below, the shaft is connected to end effector 103, but the shaft turns independently from the connection to plurality of joints 102.

Figure 1B:
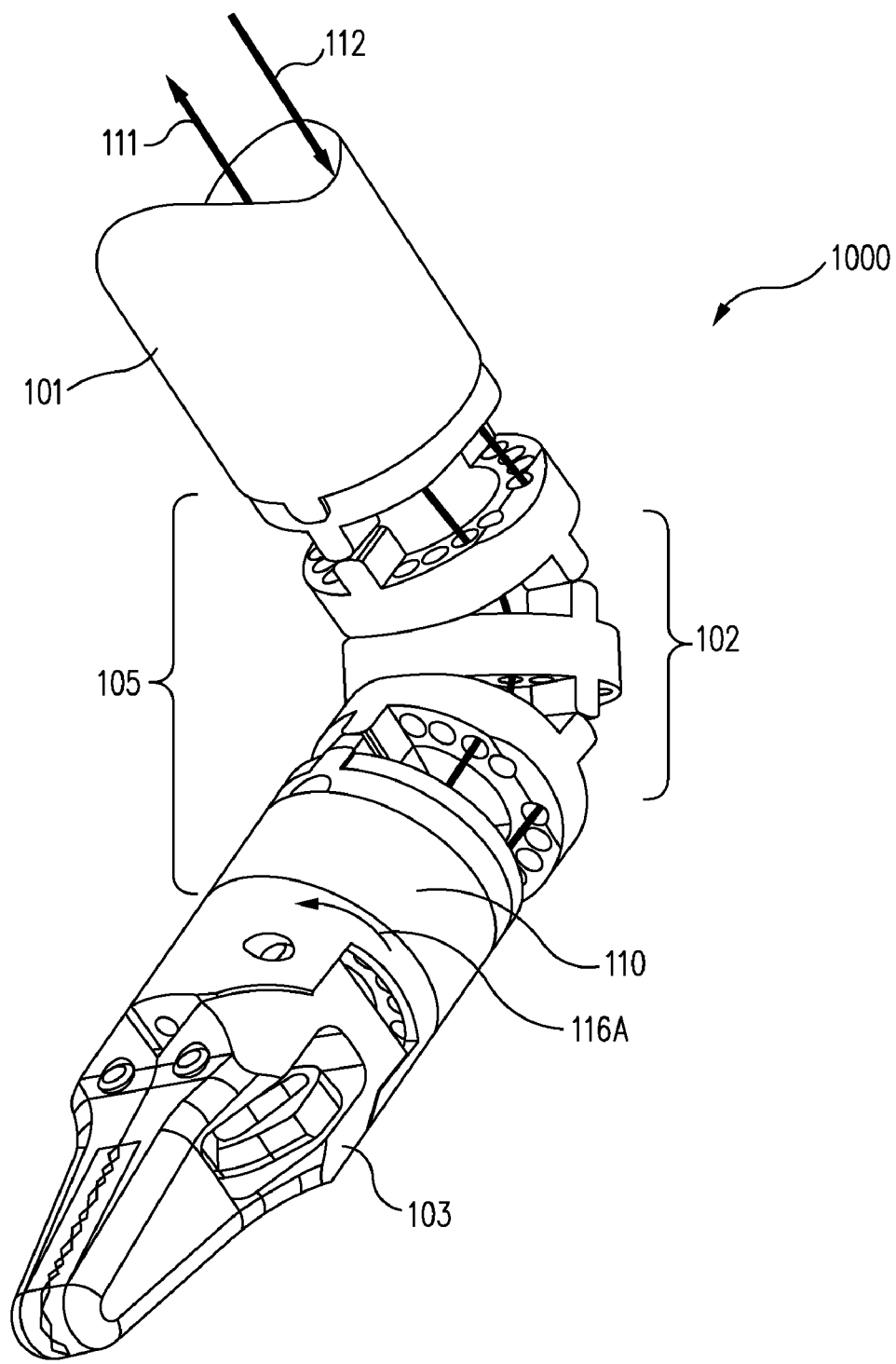

When at least a difference in tension is created in actuator tendon 111 (FIG. 1B) and actuator tendon 112, for example, by exerting a force on actuator tendon 111 relative to actuator tendon 112, the shaft rotates in a counterclockwise direction around the longitudinal axis, e.g., in a first direction, and so end effector 103 also moves in a counterclockwise direction as shown by arrow 116A. As actuator tendon 111 is pulled from the shaft, actuator tendon 112 is wound around the shaft in a counterclockwise direction.

When at least a difference in tension is created in actuator tendon 111 (FIG. 1B) and actuator tendon 112, for example, by exerting a force on actuator tendon 112 relative to actuator tendon 111, the shaft rotates in a clockwise direction around the longitudinal axis, e.g., in a second direction opposite to the first direction, and so end effector 103 also movies in a clockwise direction as shown by arrow 116B. As actuator tendon 112 is pulled from the shaft, actuator tendon 111 is wound around the shaft in a clockwise direction.

Thus, manipulation of actuator tendons 111, 112 provides distal roll for end effector 103 via compact and rigid roll joint 110 without the use of pulleys and so overcomes the prior art limitations associated with such pulleys. Moreover, the particular types of joints 102 used in wrist 105 are not of importance so long as joints 102 allow passage and manipulation of actuator tendons 111, 112 through joints 102.

Figure 2A:
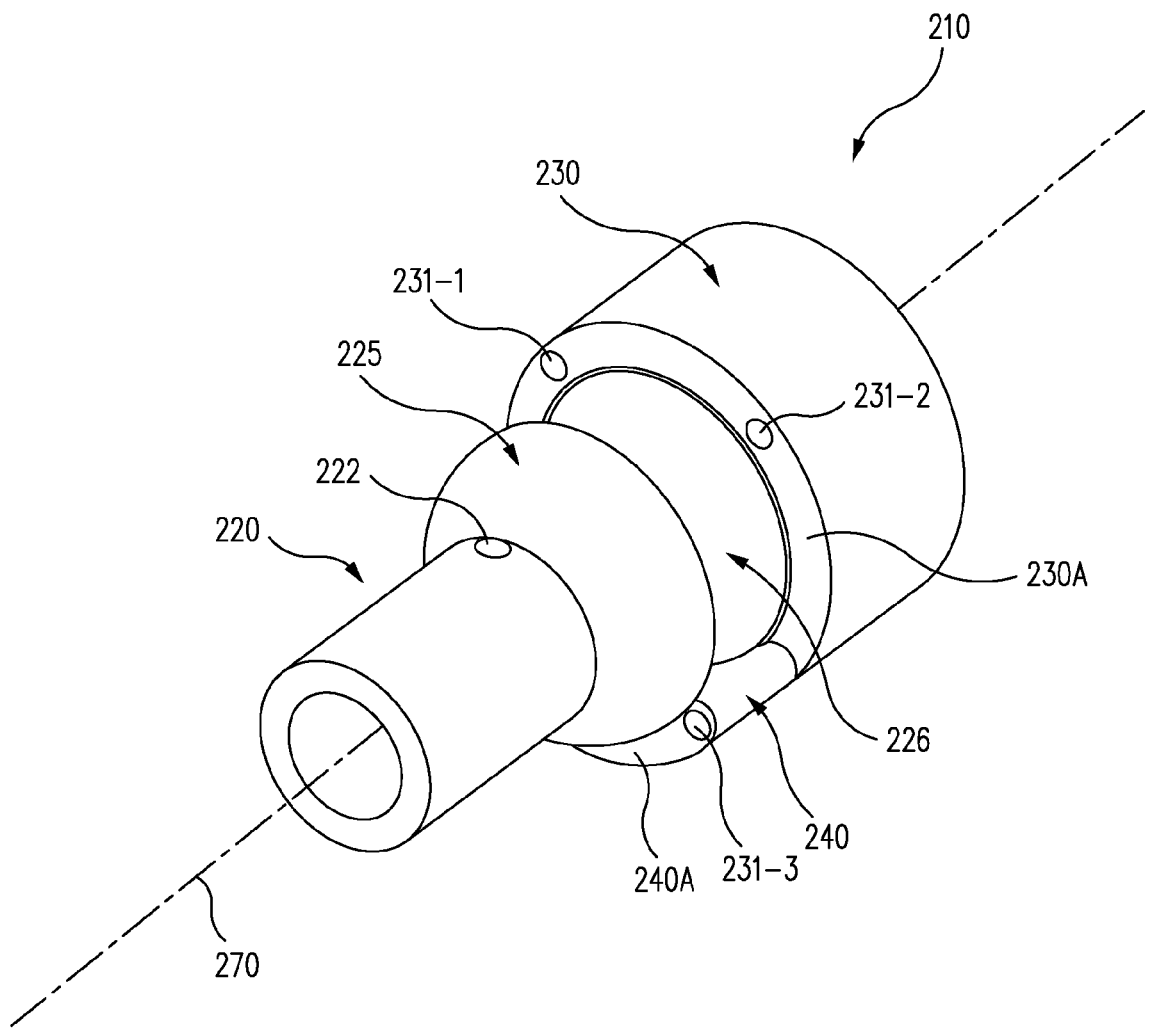
FIG. 2A is a perspective view showing the top of one implementation of the compact and rigid roll joint in FIGS. 1A to 1C.
Figure 2B:
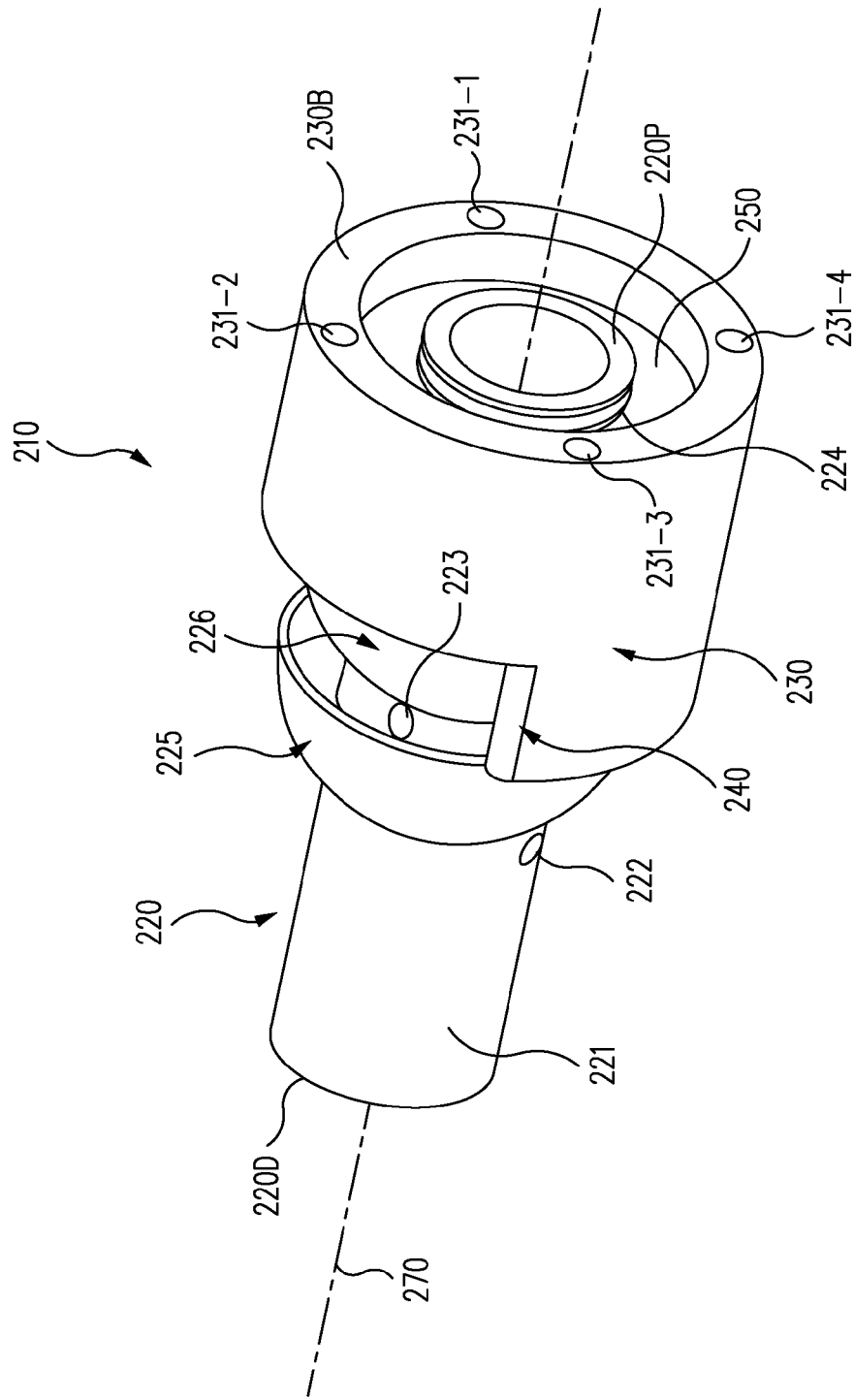
FIG. 2B is another perspective view showing the bottom of the implementation in FIG. 2A of the compact and rigid roll joint in FIGS. 1A to 1C.

FIG. 2A is a perspective view showing the top of one implementation 210 of compact and rigid roll joint 110. FIG. 2B is another perspective view showing the bottom of implementation 210 of compact and rigid roll joint 110. In FIGS. 2A and 2B, the actuator tendons are not shown.

Compact and rigid roll joint 210 includes a shaft assembly 220, a housing 230 in which shaft assembly 220 is rotatably mounted, and at least one tendon guide structure 240, which in this implementation is integral with housing 230. For ease of discussion, distal end 220D (FIG. 2B) of shaft assembly 220 is said to be at a top of roll joint 210 and proximal end 220P of shaft assembly 220 is said to be at a bottom of roll joint 210. The definition of top and a bottom is for illustration only and is not intended to limit the invention to this specific orientation.

Shaft assembly 220 includes a hollow cylindrical central shaft 221, sometimes referred to as central shaft 221 or shaft 221, about which are mounted a first tendon guide structure 225 and a second tendon guide structure 226. Shaft 221 has a distal end 220D and a proximal end 220P. A proximal direction is defined from distal end 220D to proximal end 220P.

Above and approximately adjacent an intersection of a tendon guide surface 225A of first tendon guide structure 225 (FIG. 2A) and central shaft 221 is a first through hole 222 in which one of the actuator tendons used to control the rotation of roll joint 210 is fixedly attached. When a distal end of an actuator tendon is fixed in hole 222, hole 222 is sometimes referred to as a connection point. The connection point is distal to tendon guide surface 225A.

Above and approximately adjacent an intersection of a tendon guide surface 226A of second tendon guide structure 226 (FIG. 2B) and central shaft 221 is a second through hole 223 in which the other of the actuator tendons used to control the rotation of roll joint 210 is fixedly attached. The connection point is distal to tendon guide surface 226A.

In one aspect, a centerline of hole 222 is angularly displaced 90° from a center line of hole 223 on the outer surface of central shaft 221. However, in view of this disclosure, a relative orientation of holes 222 and 223 can be selected that provides the characteristics needed for the particular roll joint. For example, in a roll joint with a limited range of travel, an orientation of holes 222 and 223 is selected to manage the minimum and maximum amounts of tendon on the drum.

Again, when a distal end of an actuator tendon is fixed in hole 223, irrespective of the method used to fix the actuator tendon in hole 223, hole 223 also is sometimes referred to as a connection point. Other examples of connection points include, for example, a connection between the actuator tendon and shaft 221 made by crimping a fitting onto the end of the actuator tendon, and inserting fitting into a notch or slot in the side of shaft 221, or a connection between the actuator tendon and shaft 221 made by passing the actuator tendon through a hole roughly tangent to the actuator tendon path around the drum. Thus, a connection point refers generally to the location on shaft 221 where the actuator tendon is coupled to shaft 221 and the connection point is distal to the actuator tendon guide surface.

At proximal end 220P of shaft assembly 220 is a circumferential groove 224 (FIG. 2B). A snap ring (not shown) is placed in groove 224 to hold proximal end plate 250 and shaft assembly 220 in housing 230.

Housing 230 includes a plurality of tendon guide channels 231-1 to 231-4, which in this aspect have a circular cross section. Each of tendon guide channels 231-1, 231-2 extends from a bottom annular surface 230B of housing 230 to a top annular surface 230A (FIG. 2A). Tendon guide channels 231-3, 231-4 extend from bottom annular surface 230B to a top surface 240A of tendon guide structure 240.

Figure 2C:
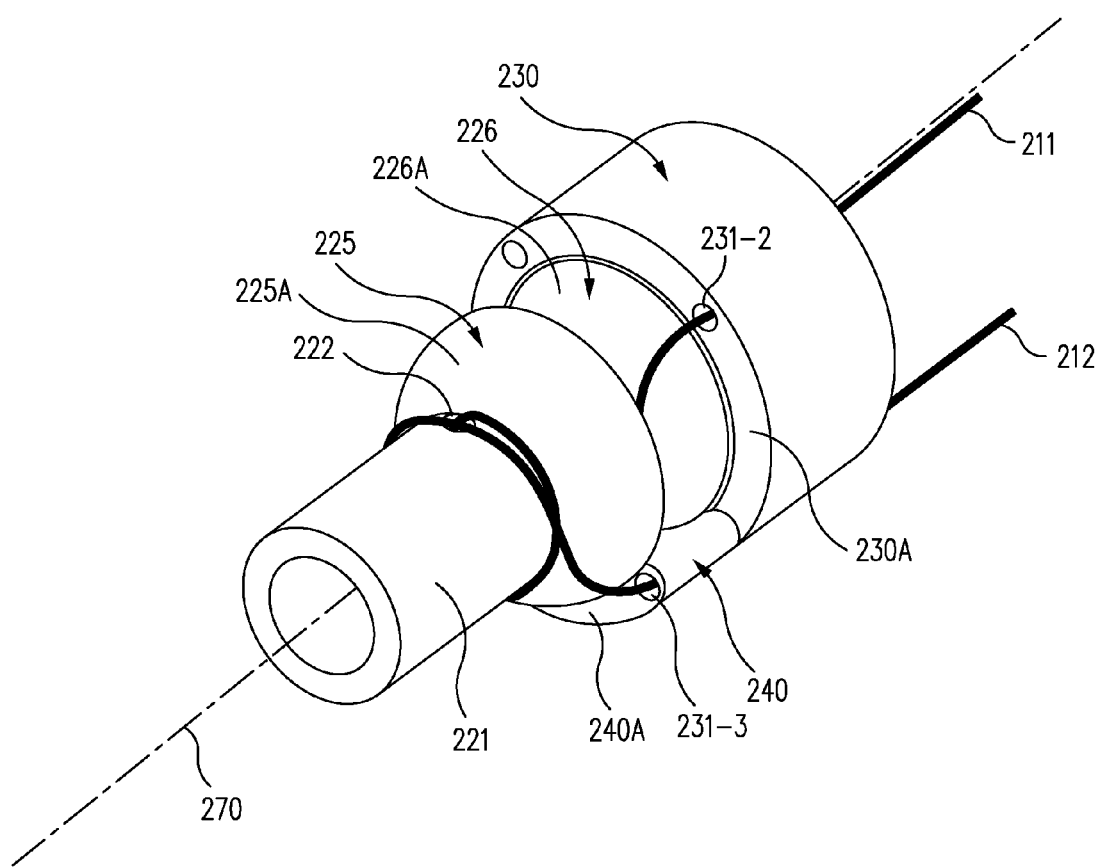
FIG. 2C is the illustration of FIG. 2A with the actuator tendons attached.

At least two of tendon guide channels 231-1 to 234-4 function as actuator tendon guides. As illustrated in FIG. 2C, actuator tendon 211 extends through tendon guide channel 232-2 and is fixedly attached to cylindrical shaft 221 in hole 223 (not shown). Similarly, actuator tendon 212 extends through tendon guide channel 231-3 and is fixedly attached to cylindrical shaft 221 in hole 222. Tendon guide channel 231-3 extends continuously through both housing 230 and integral tendon guide structure 240.

The portion of the actuator tendon in a tendon guide channel is said to be substantially parallel to longitudinal axis 270. Those knowledgeable in the field understand that manufacturing tolerances, the diameter of the actuator tendon to the diameter of the tendon guide channel, etc. affect the orientation of the actuator tendon in the tendon guide channel and so the portion of the actuator tendon in the tendon guide channel may not be exactly parallel to the longitudinal axis and so is said to be substantially parallel.

Figure 1C:
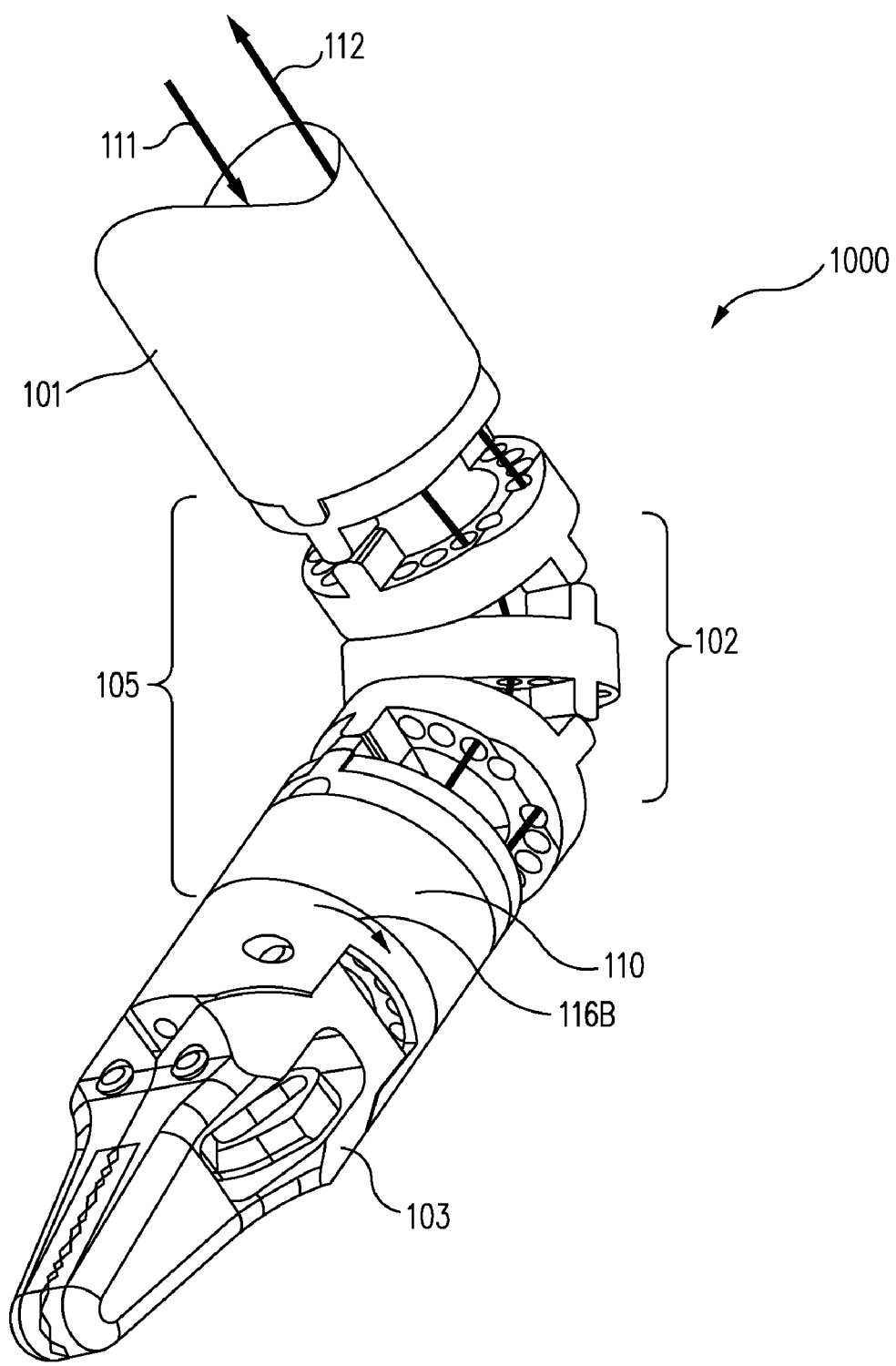

Routing the actuator tendon substantially parallel to longitudinal axis 270 is illustrative only and is not intended to be limiting to this specific aspect. In other aspects, for purposes of routing the actuator tendon back through the proximal body of the surgical instrument, e.g., surgical instrument 100 (FIG. 1), the actuator tendon can be routed along a path that is not substantially parallel to longitudinal axis 270. However, it is still useful to ensure that as the actuator tendon enters the guide channel after leaving tendon guide surface 225A, the actuator tendon is substantially tangent to a last point of contact on tendon guide surface 225A.

Tendon guide surface 225A facilitates wrapping and unwrapping of actuator tendon 211 around a portion of the outer circumferential surface of central shaft 221 referred to as a first drum. Similarly, tendon guide surface 226A facilitates wrapping and unwrapping of actuator tendon 212 around another portion of the outer circumferential surface of central shaft 221 referred to as a second drum.

As explained above, when actuator tendon 212 is drawn from roll joint 210, actuator tendon 212 is unwound from shaft 221, and shaft 221 rotates clockwise around longitudinal axis 270, which is also the axis of rotation. As shaft 221 rotates clockwise, actuator tendon 211, guided by tendon guide surface 226A, winds clockwise around shaft 221. Here, clockwise is a first direction, and counterclockwise is a second direction, where the second direction is opposite to the first direction.

Thus, roll joint 210 provides distal roll without using pulleys and utilizes tendon guide surfaces 225A, 226A to affect a transition of actuator tendons 211, 212 from having motion along longitudinal axis 270 to having motion around central shaft 221. The orientation of the actuator tendon with respect to axis of rotation 270 is changed by the tendon guide surface without the use of a pulley.

Figure 3A:
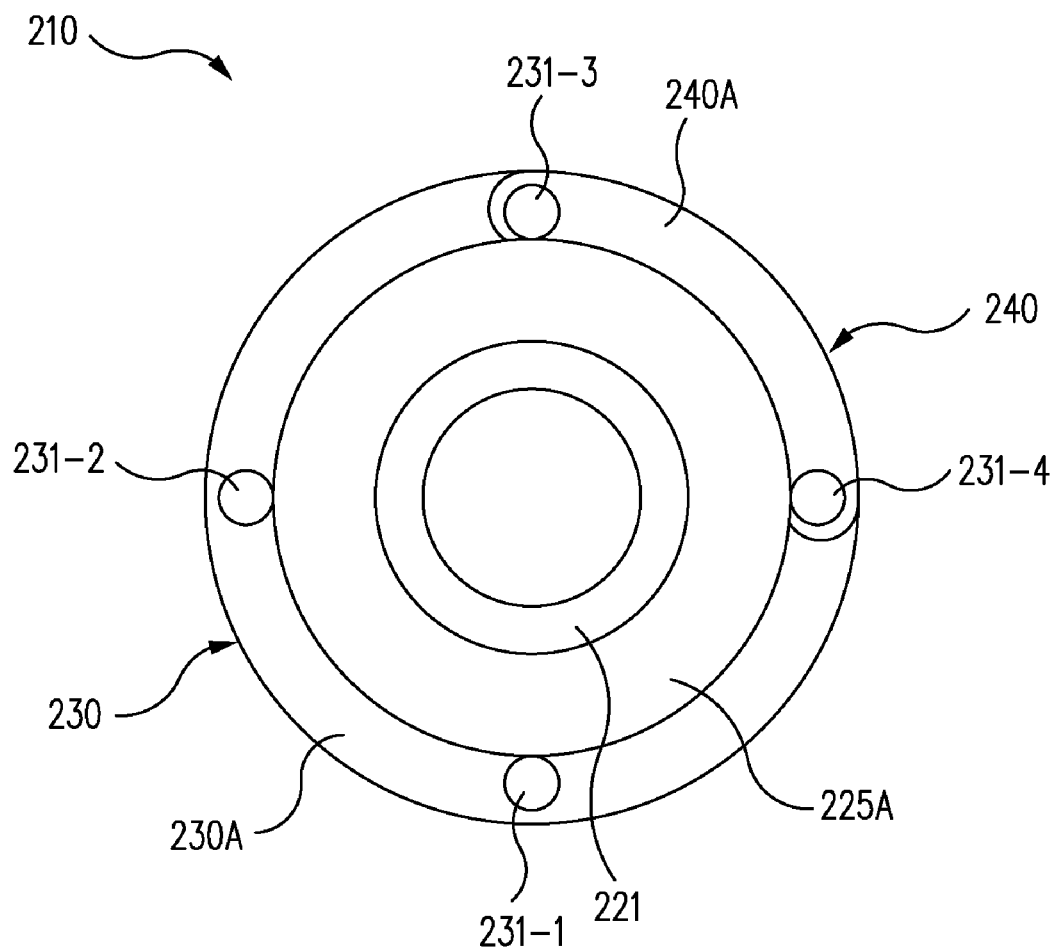
FIGS. 3A to 3C are top, side, and bottom views, respectively, for one aspect of the roll joint of FIGS. 2A to 2C.
Figure 3B:
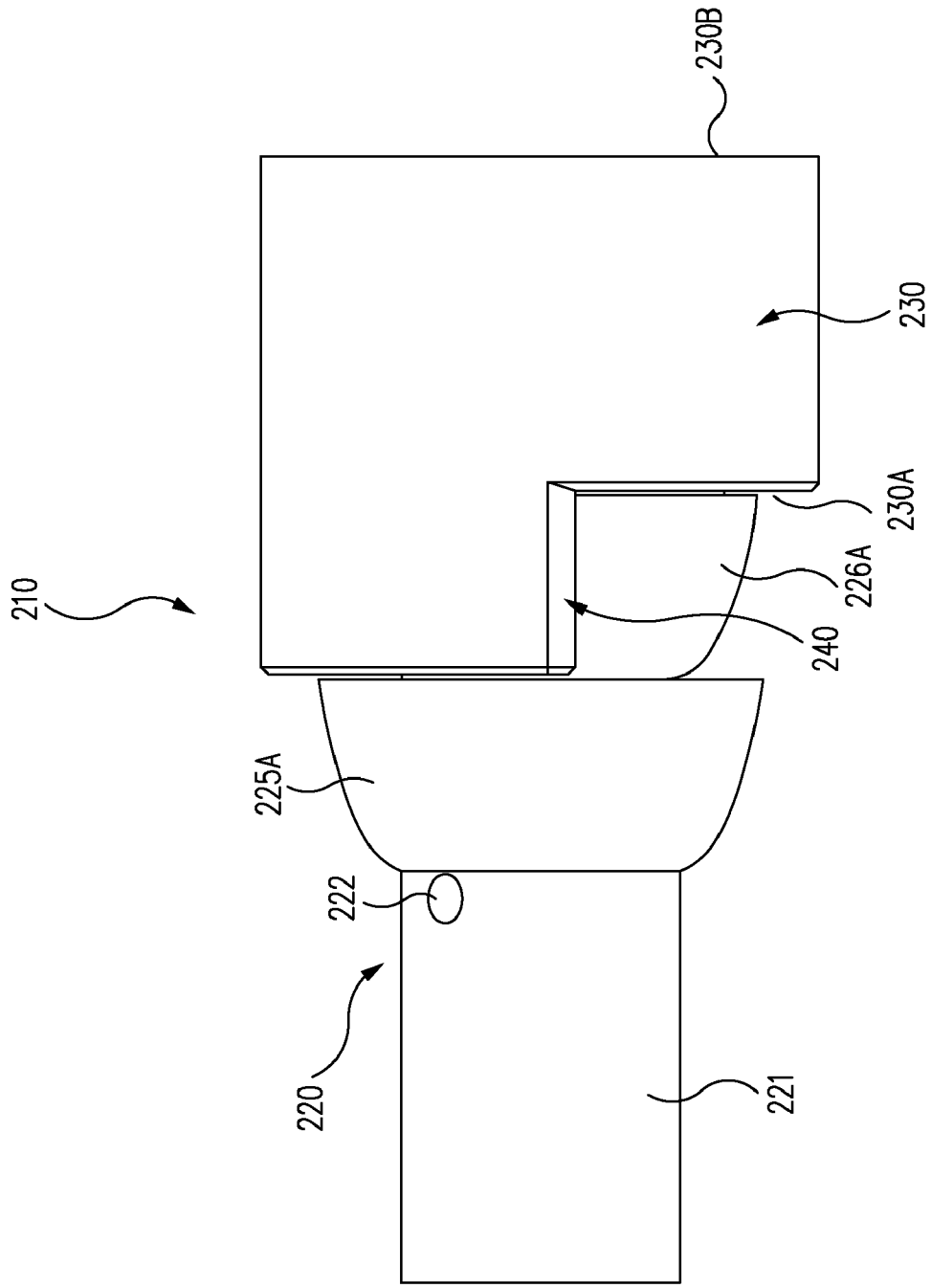
Figure 3C:
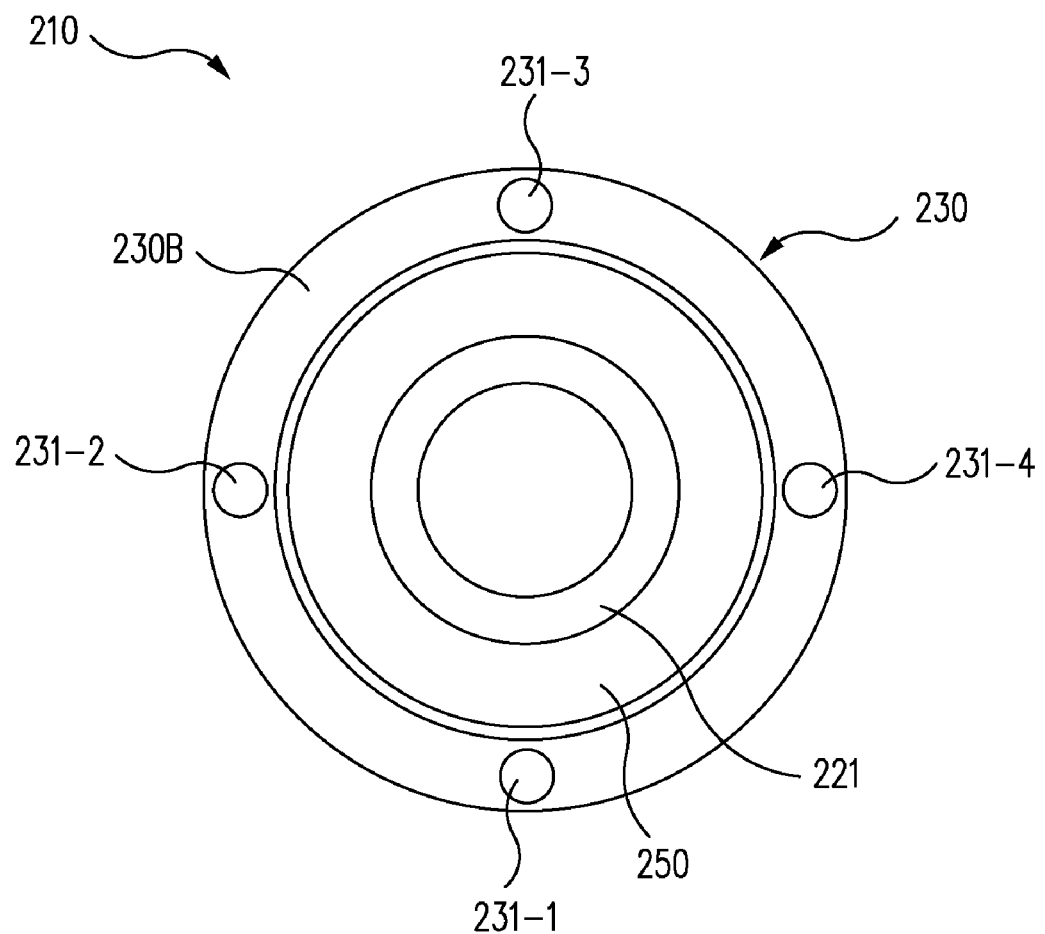

FIGS. 3A to 3C are top, side, and bottom views, respectively, for one aspect of roll joint 210. In this aspect, as shown in the top view of FIG. 3A and in the side view of FIG. 3B, tendon guide structure 240 is an arc shaped lip, which has two tendon guide channels passing there through. This shape is illustrative only, and those knowledgeable in the field can use other structures to assist in guiding the actuator tendon unto tendon guide surface 225A. The other elements in FIGS. 3A to 3C are equivalent to those described above with the same reference numeral and so that description is incorporated herein by reference for each element.

Figure 4:
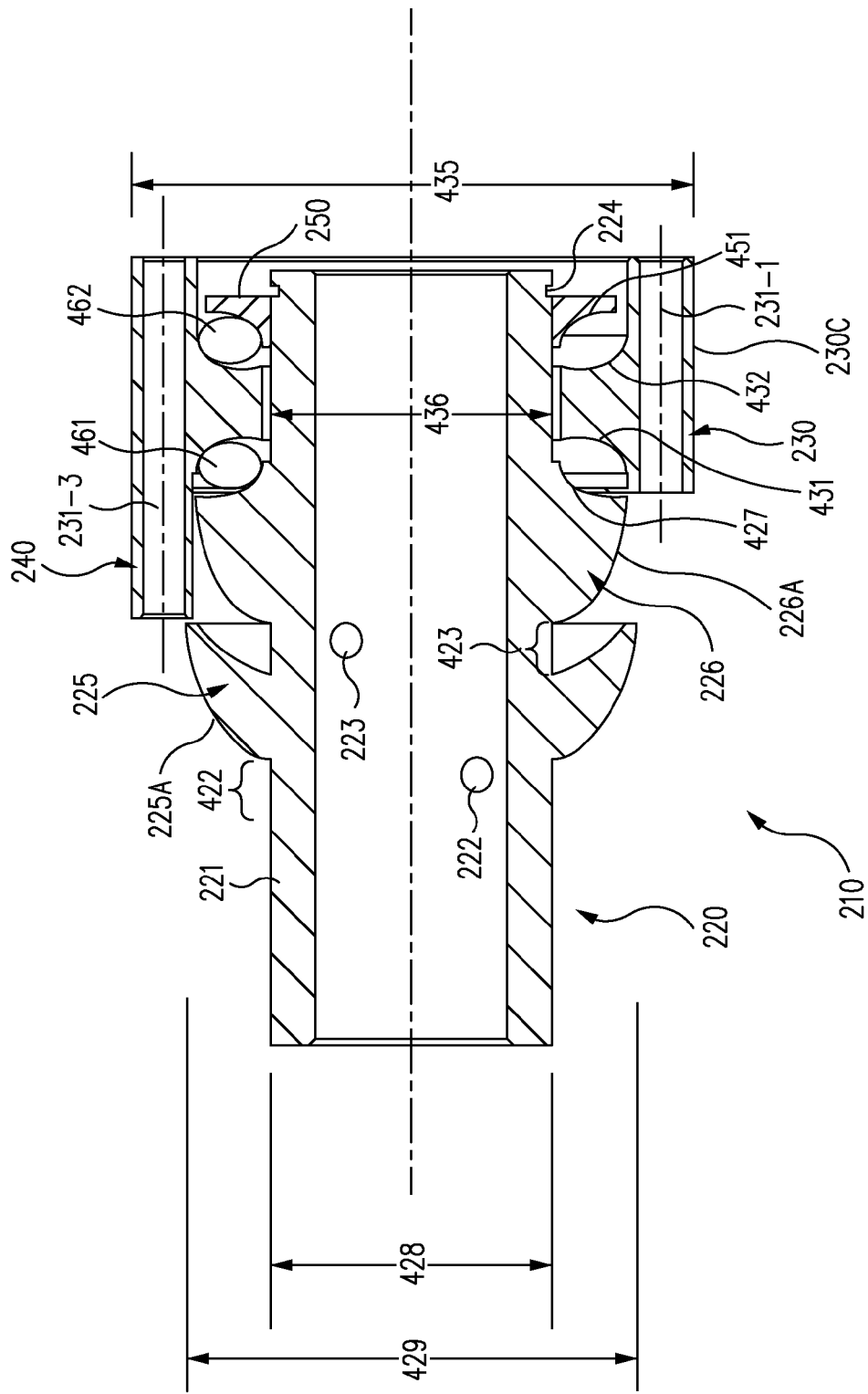
FIG. 4 is a cross-sectional cut-away view for the one aspect of the roll joint of FIGS. 2A to 2C.

FIG. 4 is a cross-sectional cut-away view of this aspect of roll joint 210. As illustrated, in this aspect, the various parts making up roll joint 210 are formed from a metal. Metals suitable for use include, but are not limited to, stainless steel or titanium. Alternatively, roll joint 210 can be formed from a plastic resin such as acetal or PEEK, which may be filled with an additive, such as glass fibers, for increased stiffness and/or strength.

The actuator tendons are typically composed of multiple strands of stainless steel wire, but the actuator tendons may be made from one or more strands of other metals or synthetic fibers such as (i) a liquid crystal polymer, sold under the trademark Vectran; (ii) ultra high molecular weight polyethylene; (iii) poly(p-phenylene-2,6-benzobisoxazole) (PBO), sold under the trademark Zylon®; or (iv) long molecular chains produced from poly-paraphenylene terephthalamide, sometimes sold under the trademark Kevlar®. However, any actuator tendon commonly used with a robotic surgical instrument can be used.

Shaft assembly 221 and housing 230 are, in this example, two concentric cylinders. The cylinder making up housing 230 has an outer circumferential surface 230C. Outer diameter 435 of housing 230 is selected so that tendon guide channels 231-1 to 231-4 can be sized to allow passage of the actuator tendons with minimal or no binding and so that tendon guide channels 231-1 to 231-4 are positioned relative to tendon guide surfaces 225A, 226A so that the actuator tendons transition from the tendon guide channels over surfaces 225A, 226A.

Each tendon guide channel has a longitudinal axis that is substantially parallel to longitudinal axis 270. The axes may not be exactly parallel due to manufacturing tolerances and the characteristics of the material or materials used to make housing 230 and so are said to be substantially parallel. Inner diameter 436 of housing 230 is selected to accommodate and support shaft 221 and any bearing structure, such as a sleeve bearing, while allowing shaft 221 to rotate freely.

Housing 230 includes a distal inner edge surface 431, e.g., a first inner edge surface which is shaped as a race for first roller bearings 461 in this aspect. Housing 230 also includes a proximal inner edge surface 432, e.g., a second inner edge surface separated and removed from the first inner edge surface, which is shaped as a race for second roller bearings 462 in this aspect.

In this aspect, tendon guide structures 225, 226 are two hemispherical structures 225, 226 that are integral with shaft 221 and have shaft 221 extending through each. Hemispherical structures 225, 226 are hemispheres with shaft 221 extending through each of the hemispheres. As used herein, fixedly attached includes being integral. Hemispherical structures 225, 226 are spaced axially apart along shaft 221. Diameter 429 of hemispherical structures 225, 226 is larger than diameter 428 of shaft 221.

A region along shaft 221 immediately above and adjacent to tendon guide surface 225A of tendon guide structure 225 is referred to as a first drum region 422. A bottom surface of tendon guide structure 225 is shaped so that a second drum region 423 is available along shaft 221 immediately above and adjacent to tendon guide surface 226A of tendon guide structure 226. A bottom surface 427 of tendon guide structure 226 is shaped as a race for bearings 461. Surfaces 225A and 226A are each an outer surface of that element.

Bottom plate 250 has an annular bottom surface and a top surface 451 shaped as a race for bearings 462.

The use of hemispheres as tendon guide structures 225, 226 is illustrative only and is not intended to be limiting to this specific structure. In view of this disclosure, those knowledgeable in the field could make surfaces 225A and 226A which would provide the desired guiding function and which would not be hemispherical surfaces. For example, surfaces 225A, 226A could be formed from triangles or trapezoids, or surfaces 225A, 226A could be continuous surfaces of non-uniform curvature. Also, it is unnecessary to use a complete hemisphere. A portion of a hemisphere would also work in some applications.

Two actuator tendons 211, 212 pass through the wall of the outer cylinder, substantially parallel to the axis of rotation, e.g., pass through tendon guide channels 231-2 and 231-3. Each of actuator tendons 211, 212 exits the tendon guide channel passes over the outer surface 225A, 226A of one of hemispherical structures 225, 226. The actuator tendon motion changes direction as the actuator tendon passes over outer surface 225A, 226A from along axis of rotation 270 to around axis of rotation 270. The actuator tendon winds, from a fraction of a turn to one or more turns, around the outer circumferential surface of shaft 221. Thus, the outer circumferential surface of the shaft forms a drum to which a tail of the actuator tendon is anchored.

As explained above, the two actuator tendons 211, 212 are wound in opposite directions. By changing the tension on one actuator tendon relative to the other actuator tendon, shaft 221 rotates around axis of rotation 270. The two outer surfaces 225A, 226A of hemispherical structures 225, 226 serve to guide the two actuator tendons 211, 212 off and on their respective drums around a longitudinal axis in a more compact space than might be required for a pair of pulleys, while using fewer parts with larger features more easily formed on a small scale, such as that of surgical instruments.

For a surgical instrument, dimensions of roll joint 210 might be a five millimeter diameter housing 230, and hemispherical structures 225, 226 with a two millimeter radius attached to a two millimeter outer diameter shaft 221. This design permits the construction of a simple and robust roll joint for a surgical instrument. Moreover, roll joint 210 can rotate shaft 221 and thus any end effector coupled to shaft 221 through multiple turns, e.g., rotations of more than 360°.

While it is not shown in the above drawings, roll joint 210 includes a mechanism for connecting shaft 221 either to an end effector or another joint, and roll joint 210 includes a mechanism for connecting housing 230 to another joint or directly to shaft 101. The two ends may be connected to other separate parts, or the features of the adjacent joints may be formed integrally into the ends of these parts. The connecting mechanisms are equivalent to those in the prior art and so are not considered further.

Figure 5A:
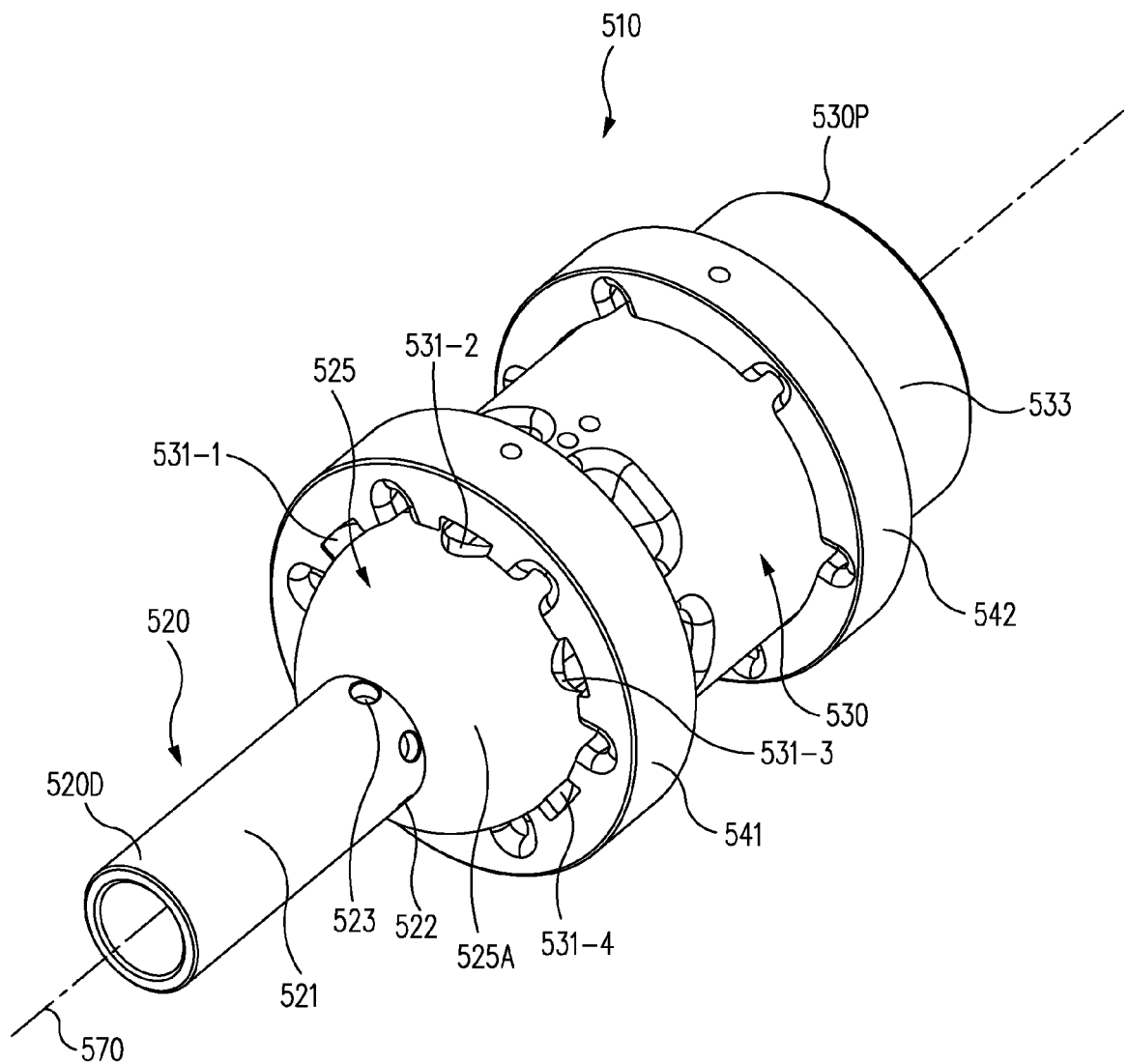
FIG. 5A is a perspective view showing the top of another implementation of the compact and rigid roll joint in FIGS. 1A to 1C that includes yaw and pitch control.
Figure 5B:
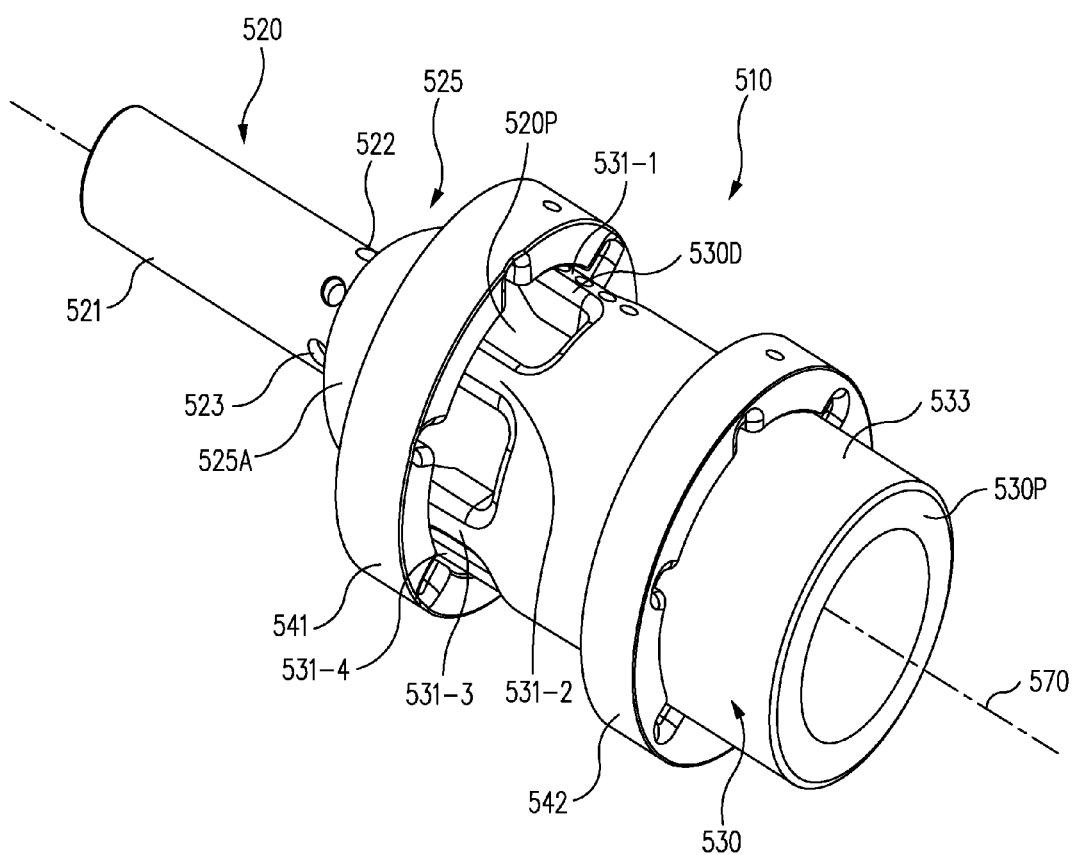
FIG. 5B is another perspective view showing the bottom of the implementation in FIG. 5A of the compact and rigid roll joint in FIGS. 1A to 1C that includes yaw and pitch control.

FIG. 5A is a first perspective view showing the top of another implementation 510 of compact and rigid roll joint 110. FIG. 5B is another perspective view showing the bottom of implementation 510 of compact and rigid roll joint 110.

Compact and rigid roll joint 510 includes a shaft assembly 520, a housing 530 in which shaft assembly 520 is rotatably mounted, and tendon guide structures 541, 542 mounted on housing 530. In addition to providing distal roll capability, compact and rigid roll joint 510 includes yaw and pitch control of distal end 520D of shaft assembly 520.

Tendon guide structures 541, 542 and housing 530 are illustrative of another aspect that provides a plurality of actuator tendon guide channels 541-1 to 541-6. While the actuator tendon guide channels are external to housing 530 in this aspect, the tendon guide channels also could have been included within housing 530 or alternatively, the housing defined to include structures 541 and 542 so that the tendon guide channels are including in the housing. The particular way used to form the actuator tendon guide channels in or on the housing is not essential and can be done in the many different ways known to those knowledgeable in the field.

For ease of discussion, distal end 520D (FIG. 5A) of shaft assembly 520 is said to be at a top of roll joint 510. Proximal end 520P (FIG. 5B) of shaft assembly 520 is mounted in a distal end 530D of housing 530. Proximal end 530P of housing 530 is said to be at a bottom of roll joint 510. The definition of top and a bottom is for illustration only and is not intended to limit the invention to this specific orientation. See also, the discussion below with respect to orientations of elements, etc.

Shaft assembly 520 includes a hollow cylindrical central shaft 521, sometimes referred to as central shaft 521 or shaft 521 that has distal end 520D and a proximal end 520P. Tendon guide structure 525 is mounted about shaft 521. In this aspect, tendon guide structure 525 is fixedly attached to shaft 521.

Also, in this aspect, tendon guide structure 525 is a portion of a sphere with shaft 521 extending into the portion of the sphere (See FIG. 7) and so is referred to as a portion of a spherical structure 525.

Above and approximately adjacent an intersection of tendon guide surface 525A of tendon guide structure 525 (FIG. 5A) and central shaft 521, i.e., distal to tendon guide surface 525A, is a first through hole 522 in which one of the actuator tendons used to control the rotation of roll joint 510 is fixedly attached. When a distal end of an actuator tendon is fixed in hole 522, hole 522 is sometimes referred to as a connection point. However, as discussed above, and incorporated herein by reference, other types of connection points can be used and so this aspect is illustrative only.

Also, above and approximately adjacent the intersection of a tendon guide surface 525A of tendon guide structure 525 (FIG. 5A) and central shaft 521 i.e., distal to tendon guide surface 525A, is a second through hole 523 in which the other of the actuator tendons used to control the rotation of roll joint 510 is fixedly attached. When a distal end, sometimes called a tail, of an actuator tendon is fixed in hole 523, hole 523 also is sometimes referred to as a connection point.

Housing 530 includes a plurality of arms 531-1 to 531-6 extending from a cylindrical portion 533. (Note arms 531-5 and 531-6 are not visible in the drawings, but are included here to indicate that in this aspect six arms are used as a part of housing 530. See FIG. 6A.)

In one aspect, each of arms 531-1 to 531-6 extends from cylindrical portion 533 of housing 530 to a point a few degrees beyond a centerline of tendon guide structure 525 so that tendon guide structure 525 is supported and movably contained by plurality of arms 531-1 to 531-6. However, tension in the actuator tendons can be used to hold tendon guide structure 525 in place so that it is not necessary that arms 531-1 to 531-6 extend exactly up to or beyond the centerline.

Tendon guide structure 541 is mounted about plurality of arms 531-1 to 531-6 so at least a tip of each of arms 531-1 to 531-6 extends through tendon guide structure 541. Tendon guide structure 542 is mounted at about a longitudinal middle of housing portion 533 in this aspect, but can be mounted at any point from the longitudinal middle to the proximal end of housing portion 533, for example. Tendon guide structure 542, in one aspect, is positioned so that actuator tendons move along housing portion 533 substantially parallel to longitudinal axis 570. In one aspect, tendon guide structure 541 is positioned to minimize interference between actuator tendons from the connection points on shaft 521 and the tips of arms 531-1 to 531-6.

Figure 5C:
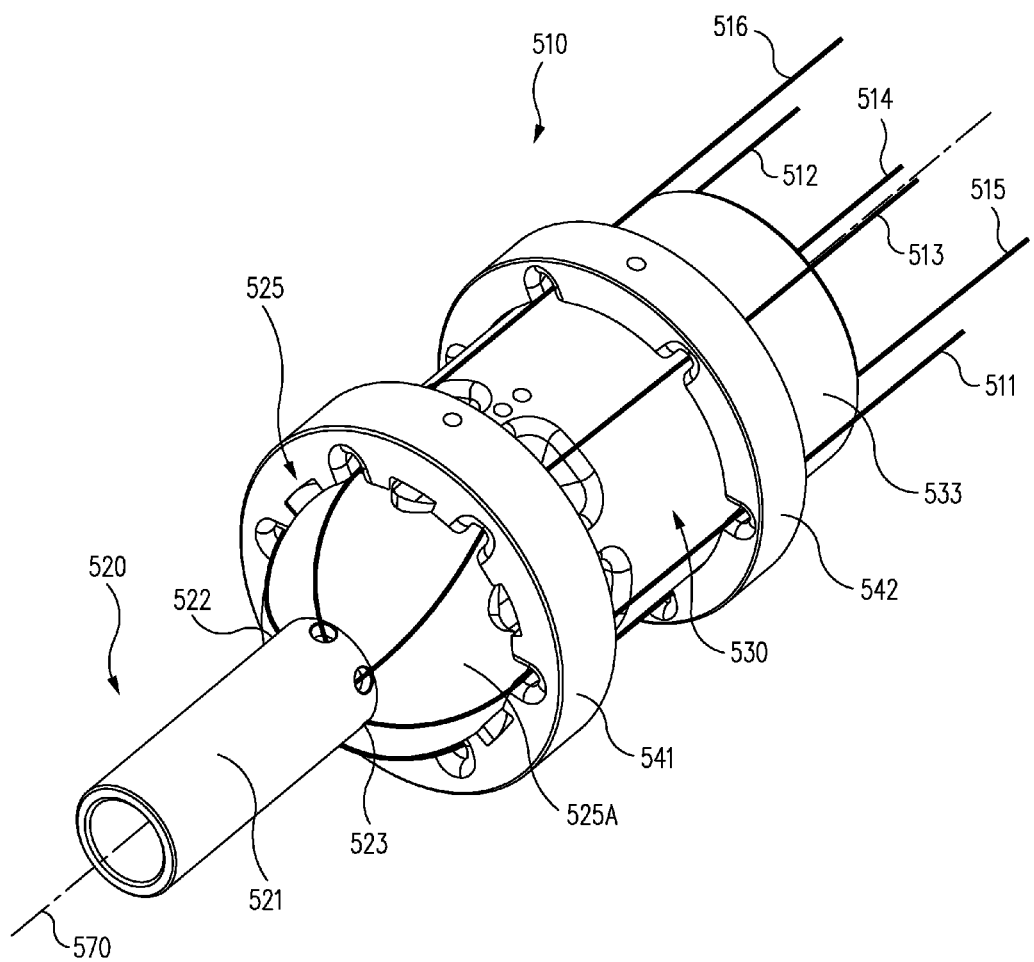
FIG. 5C is the illustration of FIG. 5A with the actuator tendons attached.

Tendon guide structures 541, 542 each include a plurality of tendon guide channels, e.g., at least one channel for each actuator tendon used for roll joint 510. At least two of the tendon guide channels in tendon guide structures 541, 542 function as actuator tendon guides for actuator tendons for distal roll. As illustrated in FIG. 5C, actuator tendon 511 extends through tendon guide channels in tendon guide structures 541, 542 and is fixedly attached to cylindrical shaft 521 in hole 523, i.e., distal to guide surface 525A. Similarly, actuator tendon 512 extends through other tendon guide channels in tendon guide structures 541, 542 and is fixedly attached to cylindrical shaft 521 in hole 522, i.e., distal to guide surface 525A.

The portion of the actuator tendon along housing portion 533 is said to be substantially parallel to longitudinal axis 570. Those knowledgeable in the field understand that manufacturing tolerances, the diameter of the actuator tendon to the diameter of the tendon guide channel, etc. affect the orientation of the actuator tendon so the portion of the actuator tendon bounded by the tendon guide channels may not be exactly parallel to the longitudinal axis and so is said to be substantially parallel.

Tendon guide surface 525A facilitates wrapping and unwrapping of actuator tendon 511 around a portion of the outer circumferential surface of central shaft 521 referred to as a drum. Similarly, tendon guide surface 525A facilitates wrapping and unwrapping of actuator tendon 512 around a portion of the outer circumferential surface of central shaft 521 also referred to as a drum. Thus, guide surface 525A changes the motion of an actuator tendon from along axis of rotation 570 to around axis of rotation 570.

When there is a difference in tension in actuator tendon 512 and actuator tendon 511 (a force is increased on tendon 512 or alternatively a force is diminished on tendon 511), actuator tendon 512 is unwound from shaft 521 and shaft 521 rotates clockwise around longitudinal axis 570, which is also the axis of rotation. As shaft 521 rotates clockwise, actuator tendon 511, guided by tendon guide surface 526A winds around shaft 521.

Thus, roll joint 520 provides distal roll without using pulleys and utilizes a tendon guide surface 525A to affect a transition of actuator tendons 511, 512 from motion along longitudinal axis 570 to motion around longitudinal axis 570 and central shaft 521. The orientation of the motion of the actuator tendon with respect to axis of rotation 570 is changed by the tendon guide surface without the use of a pulley.

In FIGS. 5A to 5C, four additional actuator tendons 513 to 516 are used with roll joint 510. One pair 513, 514 of the additional actuator tendons is fixedly attached to shaft 521 in two different through holes, just above and adjacent the intersection of shaft 521 and tendon guide surface 525A, i.e., distal to tendon guide surface 525A. In one aspect, the two different through holes are 180° apart on the outer circumferential surface of shaft 521. A difference in tension in actuator tendons 513, 514 is used to control the pitch of shaft 521.

Another pair 515, 516 of the additional actuator tendons is fixedly attached to shaft 521 in yet another two different through holes, just above and adjacent the intersection of shaft 521 and tendon guide surface 525A, i.e., distal to tendon guide surface 525A. In one aspect, the two different through holes are 180° apart on the outer circumferential surface of shaft 521. A difference in tension in actuator tendons 515, 516 is used to control the yaw of shaft 521. Because cable pairs (513, 514), (515, 516) in actuating pitch and yaw motions primarily apply moments to joint 510 about axes perpendicular to longitudinal axis 570, the range of roll motion of joint 510 is limited to a range of approximately ±90° so that the actuator tendons applying pitch and/or yaw moments continue to act along directions in which the actuator tendons may apply useful forces to roll joint 510.

Figure 6A:
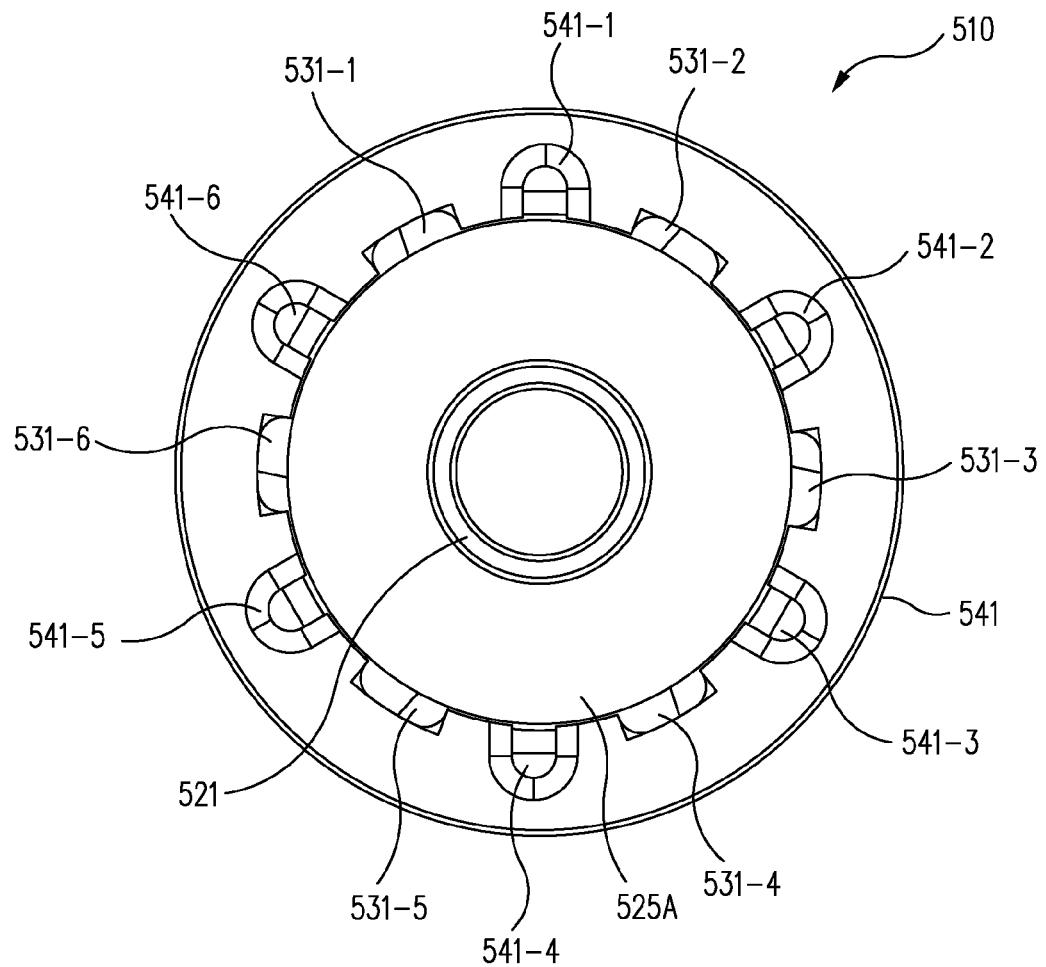
FIGS. 6A to 6C are top, side, and bottom views, respectively, for one aspect of the roll joint of FIGS. 5A to 5C.
Figure 6B:
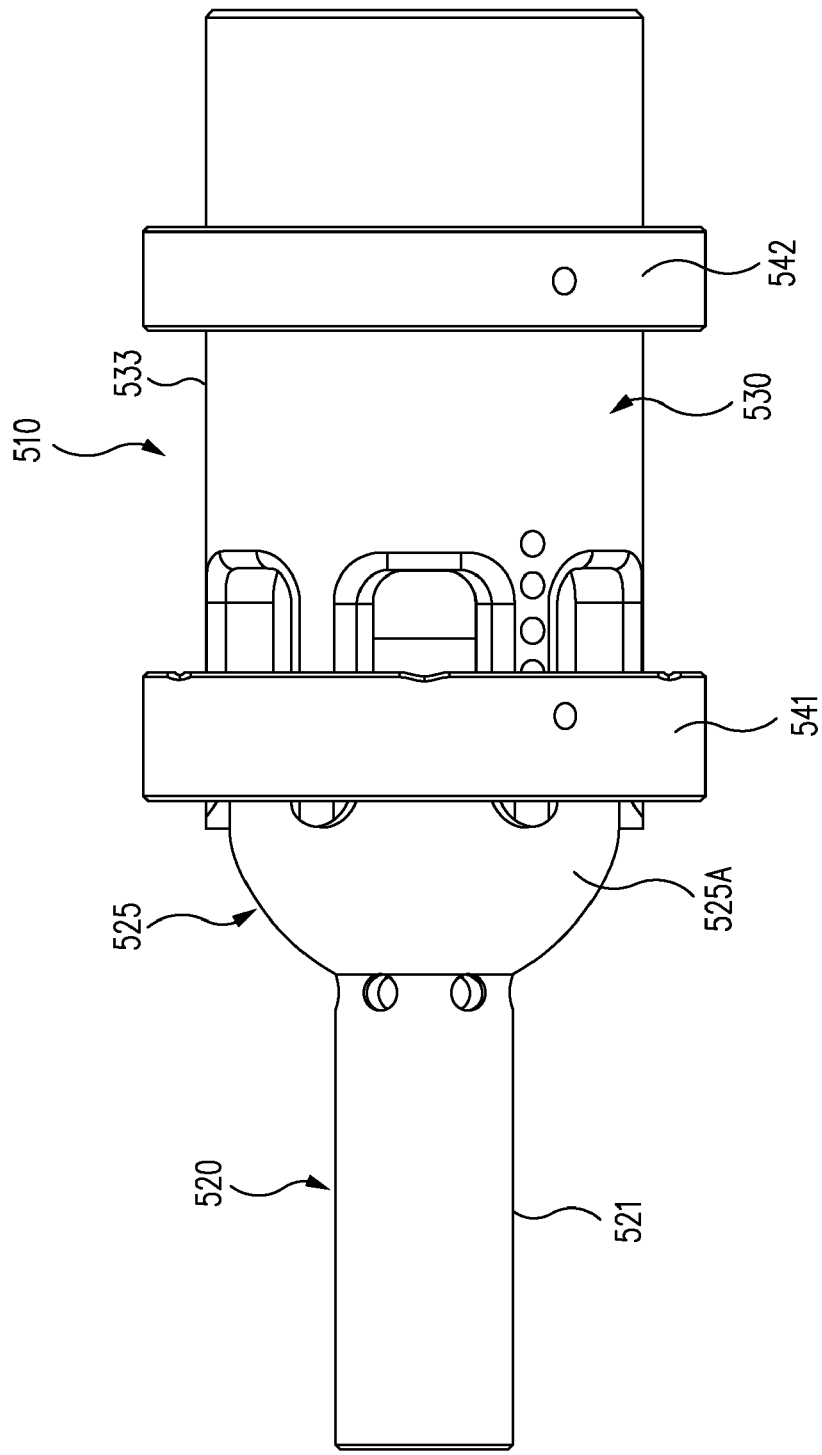
Figure 6C:
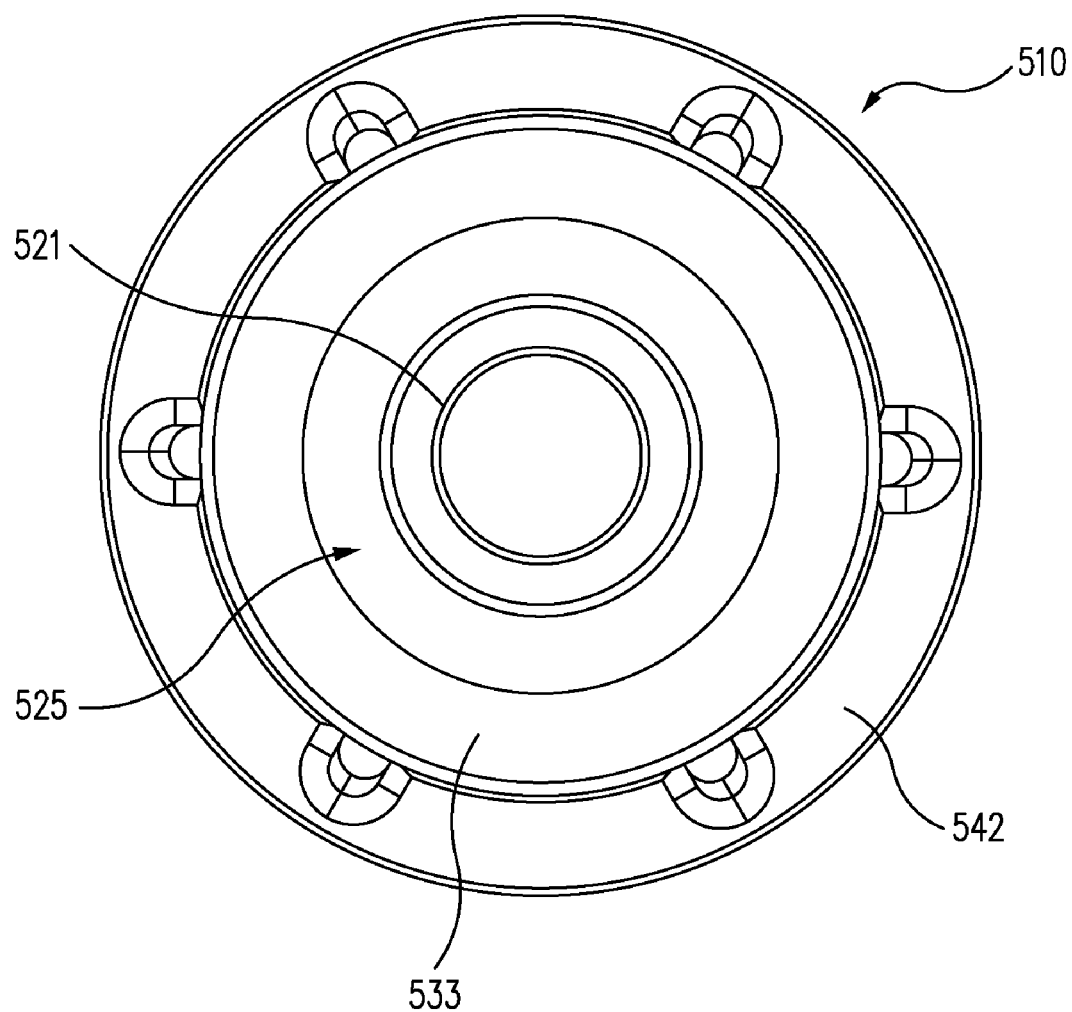

FIGS. 6A to 6C are top, side and bottom views, respectively, for roll joint 510. The elements in FIGS. 6A to 6C are equivalent to those described above with the same reference numeral and so that description is incorporated herein by reference for each element.

Figure 7:
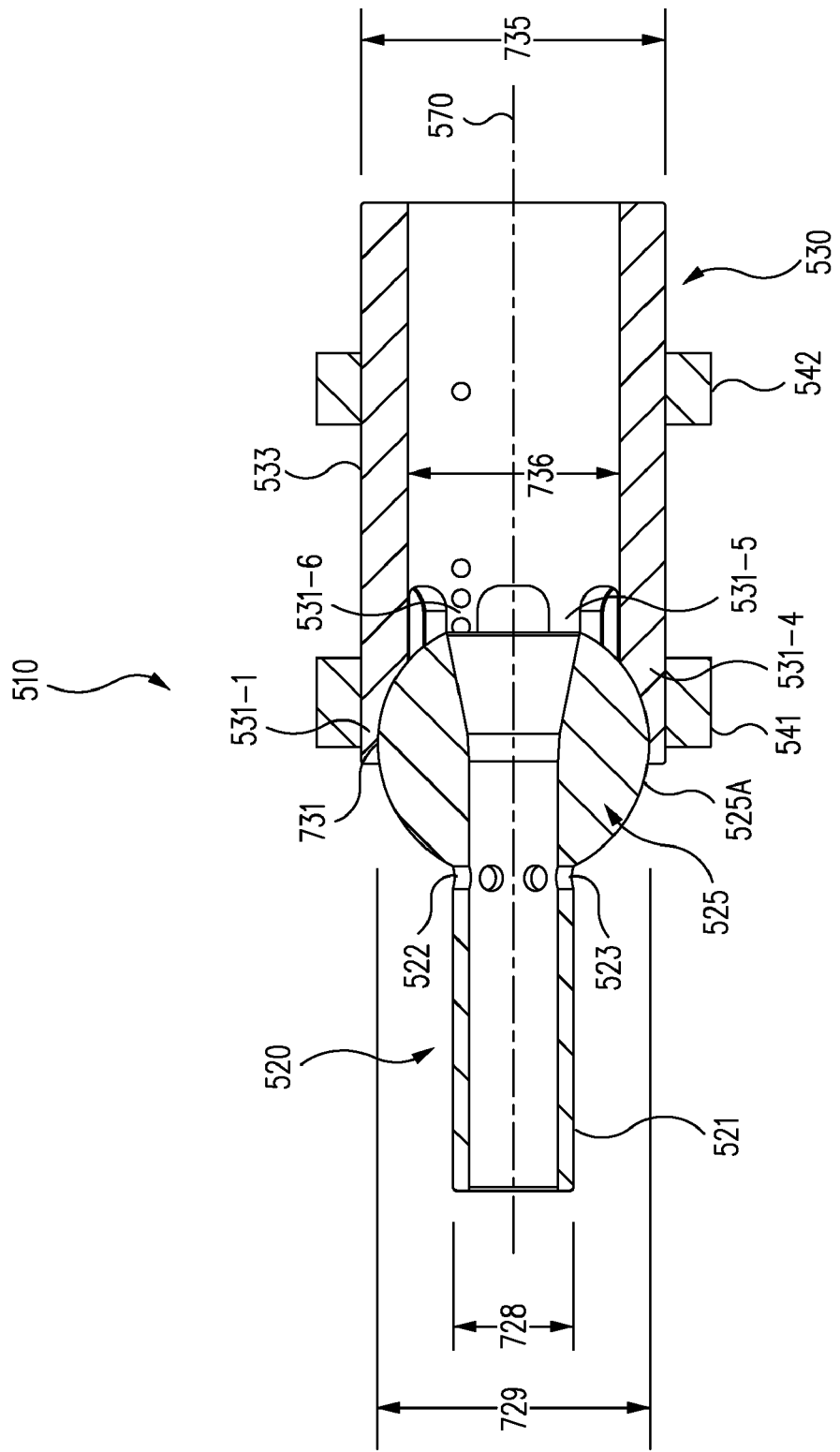
FIG. 7 is a cross-sectional cut-away view for the one aspect of the roll joint of FIGS. 6A to 6C.

FIG. 7 is a cross-sectional cut-away view of this aspect of roll joint 510. As illustrated, in this aspect, the various parts making up roll joint 510 are formed from a metal. Metals and other materials suitable for use in making roll joint 510 include those described above and that description is incorporated herein by reference. Similarly, the actuator tendons described above can also be used in this aspect.

Shaft assembly 521 and housing 530 are two concentric cylinders. Outer diameter 735 of housing 530 is selected so that tendon guide channels can be sized in tendon guide structure 541, 542 to allow passage of the actuator tendons with minimal or no binding and so that the tendon guide channels are positioned relative to tendon guide surface 525A so that the actuator tendons transition from the tendon guide channels over surface 525A.

Each arm of housing 530 includes a distal inner edge surface 731, e.g., a first inner edge surface which is shaped as a race for tendon guide structure 525. In this aspect, tendon guide structure 525 includes a portion of a spherical structure that is integral with shaft 521 and has shaft 521 extending partially through the portion of spherical structure 525. From about a center line of structure 525, the inner diameter of shaft 521 is flared out so that any actuator tendons passing through shaft 521 do not bind as the yaw and/or pitch of shaft 521 is changed. Diameter 729 of tendon guide structure 525 is larger than outer diameter 728 of shaft 521 to facilitate roll joint 510 moving through a larger range of pitch and yaw motions. Other embodiments with more restricted pitch and/or yaw motion may use a larger diameter for shaft 521.

Two actuator tendons pass through tendon guide structures 541, 542, along cylindrical portion 533 of housing 530, substantially parallel to axis of rotation 570. Each actuator tendon exits the tendon guide channel in tendon guide structure 541 and passes over outer surface 525A of spherical structure 525. The motion of the actuator tendon turns as the actuator tendon passes over outer surface 525A from along axis of rotation 570 to around axis of rotation 570, and winds around the outer circumferential surface of shaft 521. The outer circumferential surface of shaft 521 forms a drum to which a tail of the actuator tendon is anchored.

As explained above, the two actuator tendons are wound in opposite directions. By changing the tension in one actuator tendon relative to the other actuator tendon, shaft 521 is rotated. Outer surface 525A of spherical structure 525 serves to guide the two acutator tendons off of their respective drums and turn the direction of motion to along an axial direction in a more compact space than might be required for a pair of pulleys, while using overall larger parts with features more easily formed on a small scale, such as that of surgical instruments.

The use of spherical structure 525 is illustrative only and is not intended to be limiting to this specific aspect. In view of this disclosure, one knowledge in the field could make a compact roll-pitch and yaw joint with all the features of joint 510, except the roll functionally could be provided, for example, by one structure mounted on shaft 521, e.g., at least a portion of a hemispherical structure or one of the other tendon guide structures described above. The pitch and yaw functionally could be provided, for example, by a separate structure or structures mounted on shaft 521.

For a surgical instrument, dimensions for roll joint 510 might be a five millimeter diameter base, with spherical structure 525, having a two millimeter radius, attached to a two millimeter outer diameter shaft 521. This design permits the construction of a simple and robust roll joint 510 for a surgical instrument.

While it is not shown in the above drawings, roll joint 510 includes a mechanism for connecting shaft 521 either to an end effector or another joint, and roll joint 510 includes a mechanism for connecting housing 530 to another joint or directly to shaft 101. The two ends may be connected to other separate parts, or the features of the adjacent joints may be formed integrally into the ends of these parts. The connecting mechanisms are equivalent to those in the prior art and so are not considered further.

The roll joint aspects are particularly suitable for robotic surgical systems. However, a roll joint also may be included in manually operated surgical systems.

Also, the tendon guide structures are shown as being integral with the shaft. However, in other aspects, a tendon guide structure is mounted about the shaft and could, for example, be mounted such that the tendon guide structure could move relative to the shaft.

Various actuator tendon guide channels were illustrated above. In addition to those aspects, an actuator tendon guide channel could also, for example, be an open channel cut in the outer surface of the housing. Thus, as used herein, an actuator tendon guide channel is a structure associated with the housing that (i) facilitates movement of the actuator tendon along the longitudinal axis of the joint; (ii) facilitates the actuator tendon being approximately tangent to the tendon guide surface as the actuator tendon moves onto the tendon guide surface towards the drum; and (iii) facilitates the actuator tendon being approximately tangent to the tendon guide surface as the actuator tendon moves off the tendon guide surface towards the proximal end of the joint. Irrespective of the particular implementation of the actuator tendon guide channel, the actuator tendon is said to pass through that implementation.

Herein, as used in the preceding paragraph and elsewhere in this description, approximately tangent means that the actuator tendon is not required to be exactly tangent, but can deviate from exactly tangent so long as the change in direction of motion of the actuator cable from and unto the tendon guide surface is not hindered and so long as additional forces are not generated which adversely effect the rotation of the shaft assembly.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly.

Likewise, descriptions of movement along and around various axes includes various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups.

Components described as coupled may be electrically or mechanically directly coupled, or they may be indirectly coupled via one or more intermediate components. All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

We claim:

1. A roll joint comprising:
   a longitudinal axis;
   a shaft including a distal end and a proximal end, wherein a proximal direction is defined from the distal end to the proximal end along the longitudinal axis;
   a guide structure, positioned around said shaft, comprising a tendon guide surface,
      wherein said tendon guide surface intersects the shaft at a distal end of said guide structure, and
      wherein a distance between the longitudinal axis and the tendon guide surface increases as the tendon guide surfaces extends in the proximal direction from the intersection;
   a first connection point distal to the distal end of the guide structure; and
   an actuator tendon coupled to the shaft at the first connection point,
      wherein said actuator tendon wraps in a first direction around the shaft, extends from the shaft over the tendon guide surface, and extends from the tendon guide surface in said proximal direction.

2. The roll joint of claim 1 further comprising:
   a second guide structure, different from said guide structure, comprising a second tendon guide surface; and
   a second actuator tendon coupled to the shaft distal of the second guide structure, wherein said second actuator tendon wraps in a second direction around the shaft, extends from the shaft over the second tendon guide surface, and extends from the second tendon guide surface in said proximal direction, and further wherein said first direction is opposite to said second direction.

3. A roll joint comprising:
   a shaft including a distal end and a proximal end, wherein a proximal direction is defined from the distal end to the proximal end;
   a guide structure, positioned around said shaft, comprising at least a portion of a hemispherical structure,
      wherein an outer surface of the at least the portion of the hemispherical structure comprises a tendon guide surface; and
   an actuator tendon coupled to the shaft distal of the guide structure, wherein said actuator tendon wraps in a first direction around the shaft, extends from the shaft over the tendon guide surface, and extends from the tendon guide surface in said proximal direction.

4. The roll joint of claim 2 further comprising:
   a housing having said shaft rotatably mounted therein.

5. The roll joint of claim 4,
   wherein said housing includes a plurality of tendon guide channels;
   wherein said actuator tendon passes through one of said plurality of tendon guide channels; and
   wherein said second actuator tendon passes through another of said plurality of tendon guide channels.

6. The roll joint of claim 1 further comprising:
   a second actuator tendon coupled to the shaft distal of the guide structure wherein said second actuator tendon wraps in a second direction around the shaft, extends from the shaft over the tendon guide surface, and extends from the tendon guide surface in said proximal direction, and further wherein said first direction is opposite to said second direction.

7. A roll joint comprising:
   a shaft including a distal end and a proximal end, wherein a proximal direction is defined from the distal end to the proximal end;
   a guide structure, positioned around said shaft, comprising a tendon guide surface, wherein said guide structure is at least a portion of a spherical structure;
   an actuator tendon coupled to the shaft distal of the guide structure, wherein said actuator tendon wraps in a first direction around the shaft, extends from the shaft over the tendon guide surface, and extends from the tendon guide surface in said proximal direction; and
   a second actuator tendon coupled to the shaft distal of the guide structure, wherein said second actuator tendon wraps in a second direction around the shaft, extends from the shaft over the tendon guide surface, and extends from the tendon guide surface in said proximal direction, and further wherein said first direction is opposite to said second direction.

8. The roll joint of claim 6 further comprising:
   a housing having said shaft rotatably mounted therein.

9. The roll joint of claim 8,
   wherein said housing includes a plurality of tendon guide channels;
   wherein said actuator tendon passes through one of said plurality of tendon guide channels; and
   wherein said second actuator tendon passes through another of said plurality of tendon guide channels.

10. The roll joint of claim 6 further comprising:
    a third actuator tendon coupled to the shaft distal of the guide structure; and
    a fourth actuator tendon coupled to the shaft distal of the guide structure;
    wherein said third and fourth actuator tendons control yaw of said shaft.

11. The roll joint of claim 10 further comprising:
    a fifth actuator tendon coupled to the shaft distal of the guide structure; and
    a sixth actuator tendon coupled to the shaft distal of the guide structure;
    wherein said fifth and sixth actuator tendons control pitch of said shaft.

12. The roll joint of claim 6 further comprising:
    a third actuator tendon coupled to the shaft distal of the guide structure; and
    a fourth actuator tendon coupled to the shaft distal of the guide structure;
    wherein said third and fourth actuator tendons control pitch of said shaft.

13. The roll joint of claim 1, wherein said roll joint is included in a surgical instrument.

14. A method for providing distal roll in a wrist of a surgical instrument comprising:
creating a difference in tension in a first actuator tendon and a second actuator tendon,
wherein a tail of said first actuator tendon is coupled to a shaft having a distal end and a proximal end,
wherein a longitudinal axis of the wrist extends between the distal end and the proximal end, and
wherein a proximal direction is defined from the distal end to the proximal end, a tail of said second actuator tendon is coupled to said shaft, and said shaft is rotatably mounted in a housing;
unwrapping, in response to said difference in tension, said first actuator tendon from said shaft, in a first direction, over a tendon guide surface of a guide structure positioned around said shaft,
wherein said tendon guide surface intersects the shaft at a distal end of said guide structure,
wherein a distance between the longitudinal axis of the wrist and the tendon guide surface increases as the tendon guide surfaces extends in the proximal direction from the intersection, and
wherein said guide structure changes a direction of motion of said first actuator tendon; and
wrapping, in response to said difference in tension, said second actuator tendon around said shaft in said first direction.

15. The method of claim 14, wherein said wrapping includes:
wrapping said second actuator tendon around said shaft after passing the second actuator tendon over a second tendon guide surface of a second guide structure positioned around said shaft;
wherein said second guide structure changes a direction of motion of said second actuator tendon.

16. The method of claim 14 wherein said wrapping includes:
wrapping said second actuator tendon around said shaft after passing the second actuator tendon over said tendon guide surface of said guide structure;
wherein said guide structure changes a direction of motion of said second actuator tendon.

17. A roll joint comprising:
a longitudinal axis;
a first actuator tendon;
a second actuator tendon;
a housing; and
a shaft assembly rotatably mounted in said housing, said shaft assembly including:
a shaft;
a first tendon guide structure, mounted about said shaft, comprising a first tendon guide surface,
wherein said first tendon guide surface intersects the shaft at a distal end of said guide structure,
wherein a distance between the longitudinal axis and the tendon guide surface increases as the tendon guide surface extends in the proximal direction from the intersection,
wherein said first tendon guide surface guides said first actuator tendon onto a first drum region of said shaft, and
wherein said first actuator tendon wraps around said first drum region in a first direction; and
a second tendon guide structure, different from said first tendon guide structure and mounted about said shaft, comprising a second tendon guide surface,
wherein said second tendon guide surface guides said second actuator tendon onto a second drum region of said shaft,
wherein said second actuator tendon wraps around said second drum region in a second direction, and
wherein said first direction is opposite to said second direction.

18. A roll joint comprising:
a first actuator tendon;
a second actuator tendon;
a housing; and
a shaft assembly rotatably mounted in said housing, said shaft assembly including:
a shaft;
a first tendon guide structure, mounted about said shaft, comprising a first tendon guide surface,
wherein said first tendon guide surface guides said first actuator tendon onto a first drum region of said shaft,
wherein said first actuator tendon wraps around said first drum region in a first direction, and
wherein said first tendon guide structure includes at least a portion of a hemispherical structure; and
a second tendon guide structure, mounted about said shaft and different from said first tendon guide structure, comprising a second tendon guide surface;
wherein said second tendon guide surface guides said second actuator tendon onto a second drum region of said shaft,
wherein said second actuator tendon wraps around said second drum region in a second direction,
wherein said first direction is opposite to said second direction, and
wherein said second tendon guide structure includes at least a portion of a hemispherical structure.

19. The roll joint of claim 17,
wherein said housing includes a plurality of tendon guide channels,
wherein said first actuator tendon passes through one of said plurality of tendon guide channels, and
wherein said second actuator tendon passes through another of said plurality of tendon guide channels.

20. The roll joint of claim 17, wherein said roll joint is included in a surgical instrument.

* * * * *